United States Patent [19]

Kinnunen et al.

[11] 4,360,694

[45] Nov. 23, 1982

[54] PROCESS FOR PREPARING 1,2-DIACYL-SN-GLYCEROLS

[75] Inventors: Paavo K. J. Kinnunen; Tom M. Schröder; Jorma A. Virtanen, all of Espoo, Finland

[73] Assignee: KSV-Chemicals Oy, Espoo, Finland

[21] Appl. No.: 251,364

[22] Filed: Apr. 6, 1981

[30] Foreign Application Priority Data

Apr. 9, 1980 [FI] Finland ................................ 801116

[51] Int. Cl.$^3$ .......................... C09F 5/08; C11C 3/02; C07C 67/02
[52] U.S. Cl. .................................. 560/263; 560/264; 260/410.6; 260/410.7; 549/453; 549/454
[58] Field of Search .......................... 260/410.6, 410.7; 560/263, 264

[56] References Cited

U.S. PATENT DOCUMENTS

| | | | |
|---|---|---|---|
| 2,290,609 | 7/1942 | Goss | 260/410.6 |
| 3,772,357 | 11/1973 | Hamanaka | 260/410.6 |

FOREIGN PATENT DOCUMENTS

| | | | |
|---|---|---|---|
| 495548 | 8/1953 | Canada | 260/410.6 |
| 947830 | 5/1962 | United Kingdom | 260/410.6 |
| 566825 | 10/1977 | U.S.S.R. | 560/263 |

*Primary Examiner*—Paul J. Killos
*Attorney, Agent, or Firm*—Wolf, Greenfield & Sacks

[57] ABSTRACT

The object of the present invention is a novel and simple process for the production of 1,2-diacyl-sn-glycerols, wherein the acyl groups may be the same or different. According to the invention D-mannitol is reacted with benzene boronic acid or a derivative thereof to form a D-mannitol-monobenzeneboronate which compound is acylated either to form, after removal of the benzeneboronate protective group, a 1,2,5,6-tetraacyl-D-mannitol with four identical acyl groups, or is acylated selectively in two stages, by first acylating the 1,6-hydroxy groups of the boronate protected D-mannitol to form, after removal of the boronate protection, a 1,6-diacyl-D-mannitol, which then is repeatedly reacted with a benzene boronic acid or a derivative thereof and then acylated in the 2- and 5-positions. After removal of the boronate protective group, the tetra-acylated D-mannitol obtained either in the one-stage or two-stage process is split by oxidation to form a 1,2-diacyl-glyceraldehyde which in turn is reduced to the corresponding 1,2-diacyl-sn-glycerol. By means of the invention it is thus possible to prepare 1,2-diacyl-sn-glycerols in which the acyl groups can be the same or different.

15 Claims, No Drawings

PROCESS FOR PREPARING 1,2-DIACYL-SN-GLYCEROLS

The object of the present invention is a new process for preparing 1,2-diacyl-sn-glycerols of the formula

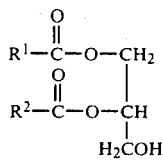

wherein $R^1$ and $R^2$ are the same or different and mean an optionally substituted, saturated or unsaturated alkyl group.

In the diacyl-glycerols found in nature $R^1$ and $R^2$ are saturated or unsaturated alkyl groups.

For scientific or clinical purposes such diacyl-glycerols or derivatives thereof may be useful, wherein either $R^1$ or $R^2$, or both, contain an easily detectable group, for example a fluorescent group such as a pyrene or an anthracene group, or a group useful for ESR-assays such as a nitroxyl group, or which is labeled with a radioactive atom.

Optically active diacyl-glycerols are conventionally prepared from D-mannitol. A typical synthesis is shown in the scheme 1 below (Pfeiffer, F. K., Miao, C. K. and Weisbach, J. Org. Chem. 35 (1970), 221)

Scheme 1

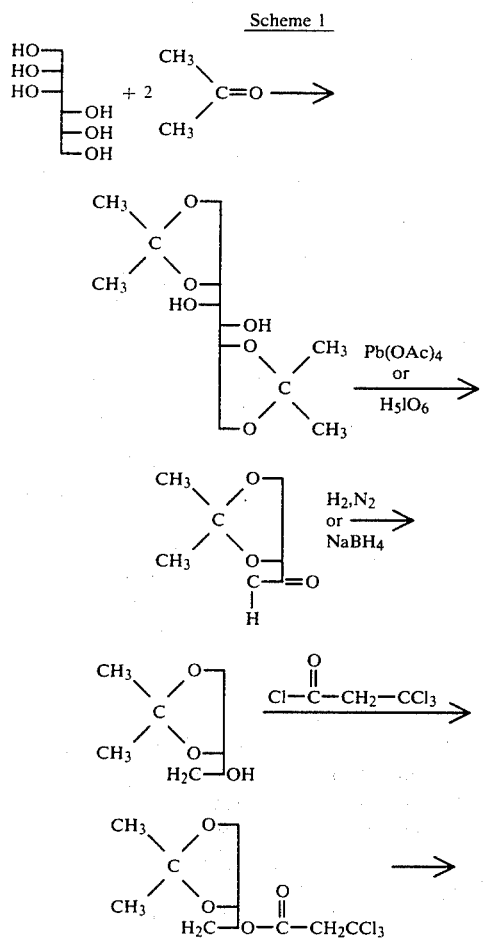

-continued
Scheme 1

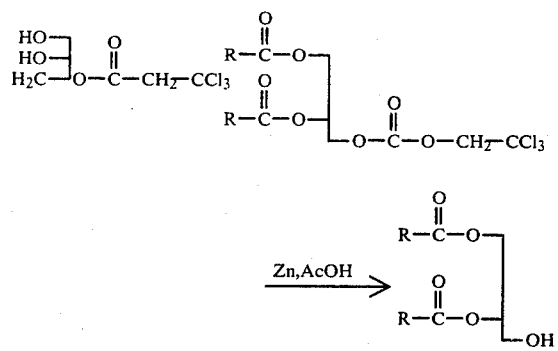

It is to be noted that by means of the above synthesis it is not possible to prepare so-called mixed acid diacyl-glyserols. The preparation of 1,2-diacyl-glycerols containing two different fatty acids is even more complicated. Buchnea (Buchnea, D., Lipids, 6 (1971)) has described a method for preparing mixed acid diacyl-glycerols which method contains twelve reaction steps.

The present invention provides a novel and simple process for preparing the compounds of the formula I given above, which process is characterized in that D-mannitol of the formula

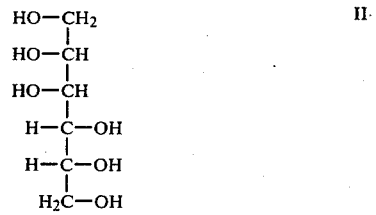

in a solvent is reacted with a benzene boronic acid of the formula

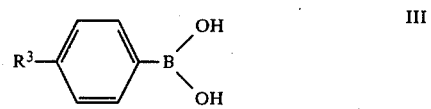

wherein $R^3$ denotes hydrogen, alkyl, alkoxy or halogen, or with a derivative thereof, and the product obtained, without prior isolation, is reacted with a functional derivative of an acid of the formula

wherein $R^1$ has the meaning given above, in the presence of a tertiary amine, the benzeneboronate protection is removed by hydrolysis or alcoholysis, whereby a 1,6-diacyl- or a 1,2,5,6-tetra-acyl-D-mannitol, respectively, is obtained having the formula

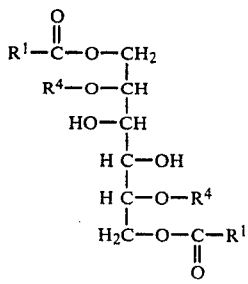

wherein $R^1$ has the meaning given above and both $R^4$ groups are either hydrogen or the acyl group

and, in order to prepare a compound of the formula I, wherein $R^1 \neq R^2$, the obtained 1,6-diacyl-compound of the formula V is reacted as described above with benzene boronic acid having the formula III or a derivative thereof, and the protected 1,6-diacyl-D-mannitol thus obtained is reacted with a functional derivative of an acid having the formula

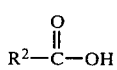

wherein $R^2$ has the meaning given above, in the presence of a tertiary amine, the benzeneboronate protection is removed by hydrolysis or alcoholysis, whereby a compound is obtained having the formula

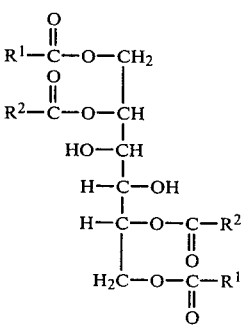

wherein $R^1 \neq R^2$, and the 1,2,5,6-tetra-acyl-compound of formula V or of the formula VII is split by oxidation and subsequently reduced with a hydride reducing agent to form the desired compounds of formula I.

In the method according to the invention the use of benzene boronic acid or p-substituted benzene boronic acid or a derivative thereof for protecting D-mannitol plays a central role.

Hitherto only tris-benzeneboronates from D-mannitol have been prepared/Suginara, J. M. and Bowman, C. M., J. Am. Chem. Soc., 80, (1958), (2443).

According to the invention it has now been found that benzene boronic acid of the formula III and its derivatives form with D-mannitol also 3,4-mono-benzene-boronates and, if in the reaction larger amounts, for example two equivalents of boronic acid, as well as higher temperatures are used, also (2,4); (3,5)-bis-benzene-boronates, which boronates are stable only in solution. The compound of the formula III may be used as the free acid or preferably as a functional derivative thereof, such as the anhydride or dichloride. The use of an anhydride is especially advantageous for the reason that less water is formed in the reaction which has to be removed before acylating. As a derivative, also D-mannitol-tris-benzeneboronate may be used, which when reacted with D-mannitol (molar ratio 1:2) forms a dry D-mannitol-3,4-monobenzeneboronate solution which does not need to be dried. As a solvent a tertiary amine such as pyridine, collidine or the like, or a solvent mixture is used, which besides a tertiary amine contains an aprotic and polar solvent, such as dimethyl formamide. The reaction temperature and reaction time are not critical, but the temperature is preferably kept low, at least before acylation, in order to minimize bis-boronate formation.

When the reaction is completed the water formed, when necessary, is removed for example by azeotropic distillation with a suitable organic solvent, such as cyclohexane, and/or drying with molecular sieves.

When acylating D-mannitol-monobenzeneboronate non-selectively, there is obtained, after removal of the protective boronate group, in good yield 1,2,5,6-tetra-acyl-D-mannitol of the formula V which then is split by oxidation to a 1,2-diacyl-glyceraldehyde, which on reducing gives the 1,2-diacyl-sn-glycerol of the formula I wherein both acyl groups are identical.

In order to prepare 1,2-diacyl-sn-glycerols of the formula I, wherein the acyl groups are different, the primary hydroxyl groups in D-mannitol are first acylated selectively. After removal of the protective boronate group, the 1,6-diacyl-D-mannitol of the formula V wherein $R^4$ is hydrogen, is isolated, the protection with benzene boronic acid is repeated, whereafter the hydroxyl groups in the 2- and 5-positions are acylated.

The oxidative splitting of the 1,2,5,6-tetracyl-D-mannitol into 1,2-diacyl-glyceraldehyde of the formula V or of the formula VII is carried out in known manner, preferably by using periodic acid, a salt thereof, or lead-tetra-acetate.

The reduction of the 1,2-diacyl-glyceraldehyde to the desired compounds of the formula I is carried out by means of a hydride reducing agent, such as sodium or potassium borohydride, in a two-phase reaction system. Such a two-phase reaction system may comprise a water-immiscible, aprotic organic solvent, such as ethylacetate, and a water solution of the hydride reducing agent. The two-phase system may also comprise the hydride in dry form together with an organic solvent, such as ethylacetate. The reaction temperature is advantageously about 0°–40° C., suitably room temperature, and the reaction time about 10 min to 3 h.

In the following scheme there is shown the reaction sequences of the invention:

Scheme 2

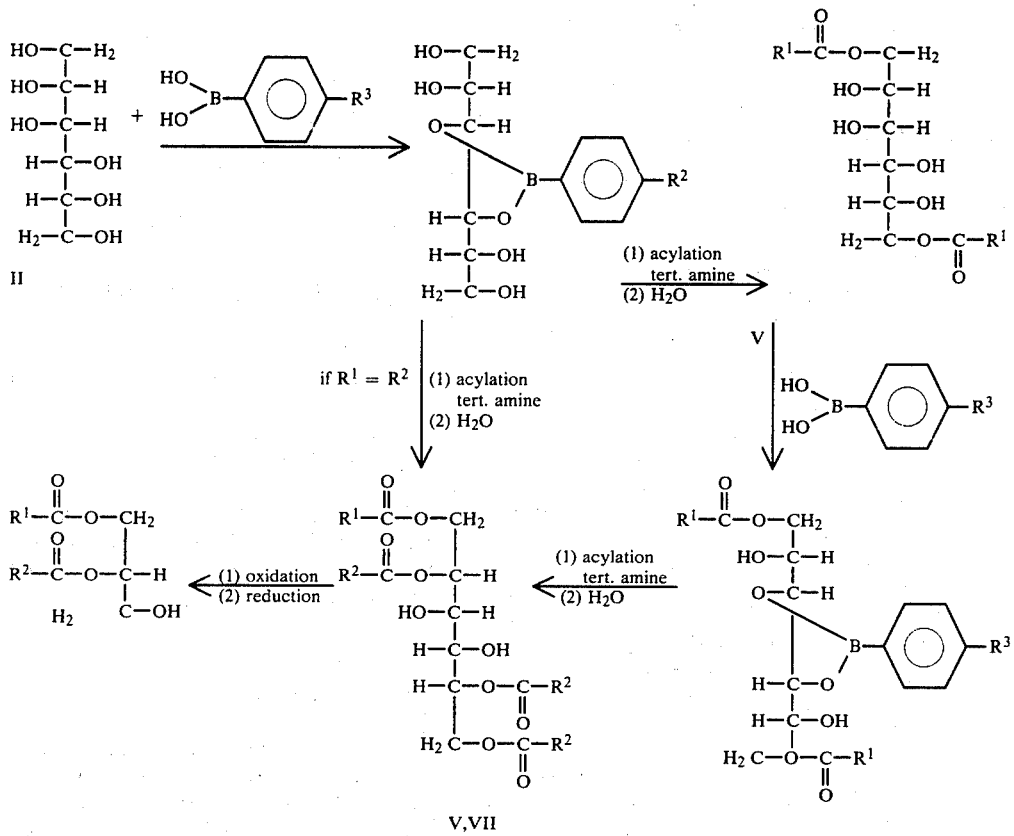

The compounds of the formula I which contain a fluorescent group, such as a pyrene or an anthracene group, or a nitroxyl group, are new compounds and as such form an object of the invention.

The following examples illustrate, but do not limit the invention.

EXAMPLE 1

1,2-dipalmitoyl-sn-glycerol (a) D-mannitol-3,4-monobenzeneboronate-solution 4.55 g of D-mannitol and 2.65 g of benzene boronic acid anhydride was dissolved in 75 ml of pyridine. 25 ml of cyclohexane was added and the cyclohexane-water-azeotrope was distilled off. 20 ml of pyridine and 5 g of molecular sieves (4 Å) were added.

The same boronate solution may also be prepared by using, instead of the benzene boronic acid anhydride, the free acid in an amount of 3.11 g.

(b) 1,2,5,6-tetra-palmitoyl-D-mannitol 40 ml (10 mmole) of D-mannitol-3,4-benzeneboronate-solution was cooled to −18° C. 11 g of palmitoyl chloride was added in 120 ml of trichloroethylene. The mixture a was left standing over night at −18° C. and at room temperature for 4 hours. The reaction mixture was washed with 240 ml of 2 N hydrochloric acid and with water. The benzeneboronate was hydrolyzed by adding 300 ml of ethanol (90%). The reaction mixture was cooled over ice and filtered. The precipitate was dissolved in 60 ml of trichloroethylene while warming slightly the mixture. The mixture was cooled and the precipitated 1,6-dipalmitoyl-D-mannitol was removed by filtration. To the filtrate 120 ml of hexane was added and the solution cooled in an ice bath. The crystallized 1,2,5,6-tetrapalmitoyl-D-mannitol was recovered by filtration. Yield 7.1 g (63%), melting point 72°–74° C.

(c) 1,2-dipalmitoyl-sn-glycerol 0.68 g of periodic acid was dissolved in 15 ml of i-propanol. This solution was added to a mixture containing 2.84 g of 1,2,5,6-tetrapalmitoyl-D-mannitol in 30 ml of trichloroethylene. After half an hour the mixture was washed with water until neutral. The solvent was evaporated in vacuum. The residue was dissolved in 50 ml of ethylacetate and reduced with 189 mg of sodium borohydride dissolved in 5 ml of water. After two hours the reaction mixture was washed with 50 ml of 0.1 N hydrochloric acid and with water until neutral. The mixture was evaporated and the residue dissolved in a small amount of a 1:1-mixture of chloroform and ethanol (90%), and fractionated on a column containing 160 g of Sephadex LH 20 using as eluent a 1:1-mixture of chloroform and ethanol (90%). The product was crystallized from hexane, yield 1.7 g, melting point 67°–68° C., $[\alpha]_b^{20} = -2.9°$ (c=1.1 in chloroform).

EXAMPLE 2

1-palmitoyl-2-oleoyl-sn-glycerol (a) 1,6-dipalmitoyl-D-mannitol

A D-mannitol-monobenzene-boronate solution was prepared as in the Example 1 but by using as a solvent dimethylformamide-pyridine at a ratio of 3:1. After removing the water as in Example 1, 40 ml of this solution was cooled on an ice bath. A cold solution containing 5.5 g of palmitoyl chloride and 2.6 ml of collidine in 20 ml of trichloroethylene was added. After four hours the mixture was washed with 80 ml of 2 N hydrochloric acid and with water. 100 ml of ethanol (90%) was added, and the mixture was kept in a refrigerator, filtered and crystallized from chloroform. Yield 4.6 g (70%), melting point 130°–131° C.

(b) 1,6-dipalmitoyl-2,5-dioleoyl-D-mannitol 3.3 g of 1,6-dipalmitoyl-D-mannitol and 0.53 of benzene boronic acid anhydride was added to a solution containing 20 ml of pyridine and 20 ml of trichloroethylene, and the mixture was dried with 5 g of molecular sieves. The mixture was cooled at −18° C. and 3.3 g of oleoyl chloride, dissolved in 10 ml of trichloroethylene, was added. The mixture was left standing over night at −18° C. and for four hours at room temperature. The reaction mixture was washed with 120 ml of 2 N hydrochloric acid and with water, and fractionated in a column containing 160 g of Sephadex LH 20 and eluting with a 1:1-mixture of chloroform and ethanol (90%), whereby the boronic acid protection was removed.

(c) 1-palmitoyl-2-oleoyl-sn-glycerol

The above compound was prepared exactly in the same manner as described in Example 1c. The product was a fluid and consequently it was not crystallized, $[\alpha]_b^{20} = -2.8°$ (c=1.0 in chloroform).

EXAMPLE 3

3.62 g of D-mannitol and 4.36 g of D-mannitol-tris-benzeneboronate were mixed with 75 ml of pyridine for 0.5 hours. Dry D-mannitol-3,4-monobenzeneboronate solution was obtained without drying.

If the D-mannitol-3,4-monobenzeneboronate solution is reacted with acylchloride according to the Example 1b the following yields are obtained for the tetracyl-D-mannitol when $R^3$ has the following meanings: $R^3$=Br, yield 55%, $R^3$=CH$_3$, yield 60% and $R^3$=OCH$_3$, yield 74%.

EXAMPLE 4

1,2-di-(4-(3-pyrenyl)-buturoyl)-sn-glycerol

According to Example 1b 40 ml of D-mannitol-3,4-monobenzeneboronate solution was reacted with 12.3 g of 4-(3-pyrenyl)-buturoylchloride, whereby 1,2,5,6-tetra-[4-(3-pyrenyl)-buturoyl]-D-mannitol was obtained, melting point ca 112° C.

According to Example 1c this was then reacted to form the desired 1,2-di-[4-(3-pyrenyl)-buturoyl]-sn-glycerol.

We claim:

1. Process for preparing 1,2-diacyl-sn-glycerols having the formula

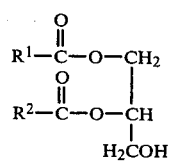

wherein $R^1$ and $R^2$ are the same or different and denote an optionally substituted saturated or unsaturated alkyl group, characterized in that D-mannitol of the formula

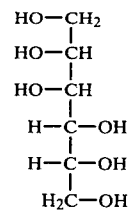

in a solvent is reacted with a benzene boronic acid of the formula

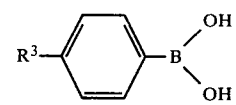

wherein $R^3$ denotes hydrogen, alkyl, alkoxy or halogen, or with a derivative thereof, and the product obtained, without prior isolation, is reacted with a functional derivative of an acid of the formula

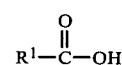

wherein $R^1$ has the meaning given above, in the presence of a tertiary amine, the benzeneboronate protection is removed by hydrolysis or alcoholysis whereby a 1,6-diacyl- or a 1,2,5,6-tetra-acyl-D-mannitol, respectively, is obtained having the formula

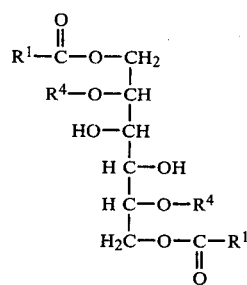

wherein $R^1$ has the meaning given above and both $R^4$ groups are either hydrogen or the acyl group

and, in order to prepare a compound of the formula I wherein $R^1 \neq R^2$ the obtained 1,6-diacyl-compound of the formula V is reacted as described above with a benzene boronic acid having the formula III or a derivative thereof and the protected 1,6-diacyl-D-mannitol thus obtained is reacted with a functional derivative of an acid having the formula

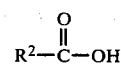

wherein R² has the meaning given above, in the presence of a tertiary amine, the benzeneboronate protection is removed by hydrolysis or alcoholysis, whereby a compound is obtained having the formula

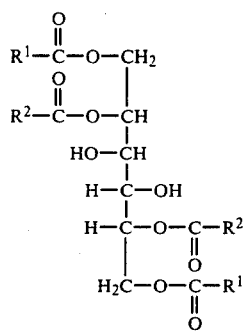

wherein R¹≠R², and the 1,2,5,6-tetracyl compound of formula V or of the formula VII is split by oxidation and subsequently reduced with a hydride reducing agent to form the desired compounds of formula I.

2. Process as claimed in claim 1, characterized in that the reaction with benzene boronic acid or with a derivative thereof, is carried out in tertiary amine or in a solvent mixture containing a tertiary amine.

3. Process as claimed in claim 1 or 2, characterized in that as a reducing agent sodium or potassium borohydride is used and the reduction is performed in a two-phase reaction system.

4. Process according to claim 3, characterized in that as the two-phase reaction system water and a water-immiscible aprotic solvent, preferably ethyl acetate, is used.

5. Process as claimed in claim 3, characterized in that as a two-phase reaction system borohydride in dry form and ethyl acetate is used.

6. In a method of preparing 1,2-diacyl-sn-glycerols, the improvement comprising reacting D-mannitol in a solvent with an optionally substituted benzene boronic acid in the presence of a tertiary amine to produce mannitol-3,4-monobenzene boronate, wherein the benzene boronate can act in subsequent reactions to protect the 3,4 mannitol sites.

7. The improvement of claim 6, further comprising esterifying said mannitol-3,4-monobenzene boronate with a first aliphatic acid.

8. The improvement of claim 7, further comprising subjecting the product of the esterification to hydrolysis to remove the benzene boronate protection, thereby producing a 1,6-diacyl-D-mannitol.

9. The improvement of claim 7, further comprising subjecting the product of the esterification to alcoholysis to remove the benzene boronate protection, thereby producing a 1,2,5,6-tetraacyl-D-mannitol in which all four acyl groups are the same.

10. The improvement of claim 8 wherein a 1,2-diacyl-sn-glycerol having two different acyl groups is desired, further comprising the steps of:
reacting said 1,6-diacyl-D-mannitol with an optionally substituted benzene boronic acid in the presence of a tertiary amine, and
esterifying the product thus obtained, without prior isolation, with a second aliphatic acid, said second aliphatic acid being different from said first aliphatic acid, thereby producing a 1,2,5,6-tetraacyl-D-mannitol in which the 1,6 acyl groups are different from the 2,5 acyl groups.

11. The improvement of claim 8, 9, or 10, further comprising the steps of:
splitting the 1,6-diacyl-D-mannitol of claim 10 or the 1,2,5,6-tetraacyl-D-mannitol of claim 11 or 12 by oxidation, and
subsequently reducing the product thus obtained with a borohydride reducing agent in a two-phase reaction system to form the desired 1,2-diacyl-sn-glycerol.

12. The improvement of claim 11, wherein said borohydride reducing agent is a compound of the group consisting of sodium borohydride and potassium borohydride.

13. The improvement of claim 11, wherein said two-phase reaction system comprises water and a water-immiscible aprotic solvent.

14. The improvement of claim 13, wherein said water-immiscible aprotic solvent is ethyl acetate.

15. The improvement of claim 11, wherein said two-phase reaction system comprises ethyl acetate and borohydride in dry form.

* * * * *